United States Patent
Calemczuk et al.

(10) Patent No.: US 10,457,908 B2
(45) Date of Patent: Oct. 29, 2019

(54) METHOD OF MICROBIOLOGICAL ANALYSIS OF A SAMPLE IN A UNIQUE CONTAINER

(71) Applicants: PRESTODIAG, Paris (FR); COMMISSARIAT A L'ENERGIE ATOMIQUE ET AUX ENERGIES ALTERNATIVES, Paris (FR); CENTRE NATIONAL DE LA RECHERCHE SCIENTIFIQUE-CNRS, Paris (FR)

(72) Inventors: Roberto Calemczuk, Grenoble (FR); David Carrara, Massy (FR); Thierry Livache, Jarrie (FR); Thibaut Mercey, Paris (FR); Félix Piat, Paris (FR); Yoann Roupioz, Goncelin (FR); Sami Slimani, Venissieux (FR)

(73) Assignees: CENTRE NATIONAL DE LA RECHERCHE SCIENTIFIQUE-CNRS, Paris (FR); PRESTODIAG, Paris (FR); COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 207 days.

(21) Appl. No.: 15/301,679

(22) PCT Filed: Apr. 3, 2015

(86) PCT No.: PCT/FR2015/050875
§ 371 (c)(1),
(2) Date: Oct. 3, 2016

(87) PCT Pub. No.: WO2015/150714
PCT Pub. Date: Oct. 8, 2015

(65) Prior Publication Data
US 2017/0022470 A1  Jan. 26, 2017

(30) Foreign Application Priority Data

Apr. 4, 2014 (FR) ...................... 14 53017

(51) Int. Cl.
*C12M 1/00* (2006.01)
*C12Q 1/06* (2006.01)
(Continued)

(52) U.S. Cl.
CPC ............ *C12M 99/00* (2013.01); *C12M 23/26* (2013.01); *C12Q 1/04* (2013.01); *C12Q 1/06* (2013.01); *C12Q 1/24* (2013.01); *G01N 33/569* (2013.01)

(58) Field of Classification Search
None
See application file for complete search history.

(56) References Cited

U.S. PATENT DOCUMENTS 5,266,486 A   11/1993 Fraatz et al.
5,518,923 A    5/1996 Berndt et al.
(Continued)

FOREIGN PATENT DOCUMENTS

| CN | 102899242 A | 1/2013 |
| WO | WO 2010/099486 A1 | 9/2010 |
| WO | WO 2012/004540 A1 | 1/2012 |

OTHER PUBLICATIONS

International Search Report issued in International Patent Application No. PCT/FR2015/050875 dated Jun. 10, 2015.

*Primary Examiner* — Rebecca L Martinez
(74) *Attorney, Agent, or Firm* — Arent Fox LLP (57) ABSTRACT

The present invention relates to a method of analysis comprising the preparation and the analysis of a sample in a flexible container without direct handling of the sample and without reopening the flexible container at the end of the (Continued)

preparation of the sample, and also to a container and a kit that enable the implementation of this method.

10 Claims, 6 Drawing Sheets

(51) Int. Cl.
*C12Q 1/24* (2006.01)
*G01N 33/569* (2006.01)
*C12Q 1/04* (2006.01)

(56) References Cited

U.S. PATENT DOCUMENTS

| | | | |
|---|---|---|---|
| 5,843,699 A | * | 12/1998 | Strenkoski ............... C12Q 1/04 435/34 |
| 2004/0009572 A1 | | 1/2004 | Felice et al. |
| 2007/0269355 A1 | * | 11/2007 | Malmqvist ............ B01F 5/0685 422/224 |
| 2008/0153153 A1 | | 6/2008 | Takenaka et al. |
| 2010/0124763 A1 | | 5/2010 | Walsh et al. |
| 2010/0216183 A1 | | 8/2010 | Okanojo et al. |
| 2013/0203634 A1 | * | 8/2013 | Jovanovich ....... B01L 3/502738 506/26 |

* cited by examiner

METHOD OF MICROBIOLOGICAL ANALYSIS OF A SAMPLE IN A UNIQUE CONTAINER

CROSS REFERENCE TO RELATED APPLICATION

This application is a 35 U.S.C. 371 National Phase of PCT Application No. PCT/FR2015/050875 filed Apr. 3, 2015, which claims priority to French Patent Application No. 1453017 filed Apr. 4, 2014. The disclosure of these applications are hereby incorporated in their entirety by reference.

The present invention relates to a method of analysis comprising the preparation and the analysis of a sample in a flexible container without direct handling of the sample and without reopening the flexible container at the end of the preparation of the sample, and also to a container and a kit that enable the implementation of this method.

Health safety is an important societal challenge. It is partly ensured by regular, standardized and often obligatory microbiological testing. Health safety relates to various fields such as food processing, the environment or health. In food processing, for example, foods and their environment are subjected to microbiological testing at various stages of production. Among the major sources of food poisoning, mention may be made, by way of examples of pathogenic microorganisms, of *Salmonella, Listeria*, and also the enterohemorrhagic strains of *Escherichia coli*.

The objective of the analyses carried out, in particular in the food-processing industry, is to obtain, as quickly as possible and completely safely, the information related to the presence/absence and/or the quantification of pathogens in a sample.

"Generic" methods of analysis exist which make it possible to detect the presence/absence of microorganisms in a sample, without distinguishing the nature of the microbial contaminant (see for example U.S. Pat. No. 5,795,773 or WO 2010/017519). In this case, it is a question of detecting the sterility or the absence of sterility of a sample. This type of generic analysis is used in the food-processing industry, for example for analyses on UHT milk, and is also commonly used in the analysis of blood, cerebrospinal fluid or urine samples, which are sterile in a healthy individual, or else in the environmental field.

On the other hand, in the case of other samples, such as food samples for example, the sample to be analyzed may naturally contain a microbiological flora in greater or lesser amount. This is in particular the case in most transformed or non-transformed dairy products. In order to verify the safety of such a product, it is then necessary to specifically search for the presence of pathogenic bacterial species within the total microbiological flora. For example, Listeria will often be looked for in a cheese, and *Salmonella* will often be looked for in poultry meat.

The quantitative aspect is also important since it may be necessary to evaluate the concentration of a category of microorganisms of interest in a sample such as a food. These data vary from one pathogen to another (cf. regulation no 2073/2005 of the official journal of the European Union).

In order to perform this search for pathogenic bacteria in a sample, it is usually necessary to disperse and/or dilute the sample in an appropriate liquid culture medium (generally to ¹⁄₁₀th), in a container. The sample is therefore weighed, the amount of appropriate enrichment liquid is added, and then the whole mixture is homogenized. This homogenization is required in order to guarantee dispersion of the food matrix in the culture medium and uniform distribution of the microorganisms sought. This step is generally carried out by virtue of a manual or mechanical action through flexible containers (bags) which allow homogenization. All of these steps (weighing, dilution, homogenization) represent the "preparation of the sample". The mixture obtained is then incubated at a given temperature (usually 37° C.), for a given period of time (usually overnight) allowing the microorganisms being sought to multiply, which is referred to as the "enrichment phase". At the end of this enrichment phase, a sample is generally taken by opening the container, in order to carry out the subsequent analysis of the sample outside the container; this analysis may for example be the detection of a pathogenic bacterium. In the case of solid or semi-solid samples, it may be useful to use a filter, sometimes directly included in the bag, which will make it possible to retain the solid particles that might impair the analysis or the sampling that will enable the analysis, while at the same time allowing the microorganisms to pass through.

The obtaining of a result therefore requires a series of time-consuming and labor-consuming operations and manipulations and is a source of possible risks (for example contamination of the operator, of the working environment or of the sample) or a source of errors. Furthermore, it is advantageous for manufacturers to be able to have the results of these analyses as early as possible. However, since the detection of the microorganisms being sought is carried out at the end of the enrichment period, the result can only be obtained at the end of this enrichment phase and of the detection phases which follow it.

Document FR 2691374 describes a filtering bag consisting of two walls made of deformable material 1 and 2 and of a filter 3 which are sealed together along three edges, the fourth edge being left open so as to form a bag. The filter is sealed between the two walls so as to form two compartments, one containing the crude mixture solution and the other containing the filtrate. This bag needs to be opened in order to take a sample and then perform an analysis. This operation is difficult to automate and increases the risk of contamination of the sample and of the handler.

Document FR 2938449 presents a filter bag for microbiology having a pipe that enables the filtrate to be brought up to the open side of the bag and thus to sample it simply. In this device, the bag is not closed, and it must be open in order to allow the filtrate to travel up the pipe. In addition, the pipe does not make it possible to easily dispense the content of the bag or to connect thereto a sensor or an automatic sampling system in a leaktight manner.

Document U.S. Pat. No. 5,266,486 presents a container for detecting microorganisms present in a sample, for example a blood sample, by detecting metabolites resulting from the growth of these microorganisms. Although this container makes it possible to indirectly detect the presence of bacteria, optionally without having to open it, it does not allow mechanical homogenization of the sample to be analyzed since this container is necessarily solid. This therefore limits its use to liquid samples.

Document WO 2004/092401 describes a method for the detection of bacteria present in a sample and also a detection device capable of specifically detecting bacteria present in a sample during the enrichment phase without any sampling carried out by the operator. However, this method has several drawbacks: it requires the bag to be opened after homogenization in order to introduce therein the detection device, the device not being suitable for mechanical homogenization apparatuses; furthermore, it requires a control of the temperatures which must be different in the two compartments of the device.

Document WO 2012/004540 describes a method for the specific detection of microorganisms in a sample during the enrichment phase. In this method, a biosensor is sealed in a flexible plastic container or immersed in the culture medium. Since the sensor is sealed at the level of the sample, it is not possible to homogenize the content of the bag without the risk of damaging the sensor or of impairing the homogenization. In the second alternative proposed in document WO 2012/004540, the biosensor must be enclosed in the bag. This imposes constraints on communication with the exterior, in particular because the position of the biosensor in the bag is not reproducible.

WO 2011/133694 describes an electrochemical method and also a specific device for the detection of *Salmonella enterica* by using aptamers. However, this device, which uses a rigid sample container, also requires prior homogenization of the sample, especially if said sample is solid or semi-solid, and the intervention of an operator in order to carry out the transfer of the suspension to be analyzed into the container. It does not therefore make it possible to carry out the successive preparation and enrichment steps in the same container, without opening the latter at the end of the homogenization of the sample.

There is therefore no process for preparing, transporting, diluting, homogenizing and analyzing a solid or semi-solid sample that can be easily automated and reduces the risks of contamination.

The Applicant has developed a method of analysis of a sample which makes it possible to overcome the drawbacks of the methods known up until now. Thus, the present invention relates to a method of analysis of a sample, to a flexible container, and also to an analysis kit.

The method of analysis of a sample according to the invention comprises:
a) the introduction of the sample and of a culture medium into a flexible container;
b) the homogenization of the sample and of the culture medium so as to obtain a homogenized mixture;
c) the enrichment of the homogenized mixture; and
d) the analysis of the homogenized mixture by an analysis system;
characterized in that
steps a) to c) are carried out in a single container;
the flexible container is closed at the end of either of steps a) and b);
a module is connected to the flexible container at the start, during or at the end of step c); and
steps c) and d) and the connecting of the module to the flexible container are carried out without requiring reopening of the container.

According to the invention, the homogenization is not only a homogenization by simple agitation of the container and/or the content. The term "homogenization" is also intended to mean homogenization of the content by mechanical deformation of the container. Such homogenization by mechanical deformation of the container encompasses crushing, milling, kneading and mixing operations when the content is solid, semi-solid or pasty, but also operations for mixing liquids or suspensions.

According to one embodiment, several containers are connected to a module during the analysis method, thus allowing simultaneous analysis of the mixtures contained in each of the containers.

This method has the advantage of carrying out all the steps in a single container, including the homogenization of the sample, without requiring reopening of the container after the enrichment step. Thus, the number of interventions by an operator and the exposure of the operator to the homogenized mixture once enriched can be reduced, thereby making it possible to limit the risks of contamination and also to more easily automate the process. This method can also be easily automated, because the container does not need to be reopened once the enrichment step has begun. It is thus possible to easily handle the bags with an automated device and to carry out the collection and/or analysis operations, whereas they are today performed essentially manually because of the necessary reopening of the container.

In step a) of preparation of the sample, a sample to be analyzed which has a given molecular weight is introduced into a flexible container.

The nature and the consistency of the sample to be analyzed are not particularly limited. The sample may be liquid or at least partly pasty or solid. The sample may for example be derived from food-processing products such as meat-based products, fish-based products, dairy products, egg-based products or plant products. It may also be environmental specimens (production water, working surfaces) or primary production samples (animal feces, boot swabs, water from hatcheries). The sample may also come from human specimens (blood, urine, feces, pulmonary expectorations, etc.) or samples from the cosmetics and pharmaceutical industry. A culture medium is added to the sample. The culture medium is chosen from the most suitable culture media so as to promote the development of the target analyte. By way of nonlimiting examples, the culture medium can be chosen from buffered peptone water (BPW), tryptic soy casein broth (TSB), brain-heart infusion broth (BHI), Demi-Fraser broth and Bolton broth.

The flexible container may be any flexible container suitable in particular for mechanical homogenization. For the purposes of the present invention, the term "flexible container" or "bag" is defined in particular as a container made of flexible material, such as a flexible plastic, and which opens at the top. Typically, the container of the present invention comprises two polygonal, preferably essentially rectangular, plastic sheets. Said sheets are sealed to one another by their sides, one side of the sheets being free to form the opening. The side of the container that has the opening is defined as the top of the container. The side opposite the opening is defined as the bottom of the container. The remaining sides are defined as the lateral sides of the container. In the remainder of the description, an upper part of the container will refer to a part of the container located on the side of the opening and a lower part of the container will refer to a part of the container located on the side of the bottom of the container. The bottom of the container can form a bellows. However, in order to enable ideal homogenization, the bottom of the container does not exhibit bellows and is formed from a simple sealing of two plastic sheets. The container of the present invention is for example a container of homogenization bag type suitable for homogenization apparatuses of Stomacher® bag type. The container preferably has a height to width ratio of between 1 and 2.5. For example, the dimensions of the container are chosen from a height of between 12 and 18 cm for a width of between 7 and 12 cm (15×10±2 cm), a height of between 25 and 35 cm for a width of between 14 and 24 cm (30×19±5 cm), and a height of between 48 and 68 cm for a width of between 28 and 48 cm (58×38±10 cm).

The opening of the container must be sufficiently large to allow the introduction of the sample to be analyzed into the container. It must allow the flexible container to be filled with liquid, semi-solid or solid materials. This opening may have a perimeter of more than 2 cm, or even 5 cm, 10 cm, or more than 15 cm, depending on the size of the sample to be analyzed. It may be located on all or part of the upper side of the container.

The flexible container must, moreover, be able to be connected to a module without requiring reopening of the container at the end of the enrichment step. The term "reopening of the container" is intended to mean an action on the container which results in exposure of the content of the container to the outside environment. The term "module" is intended to mean an analysis system that can be directly connected to the flexible container or a collection system for the purpose of a subsequent analysis.

Thus, the container comprises a socket. For the purposes of the present invention, the term "socket" is intended to mean a rigid mechanical means which has a connecting element that makes it possible to physically link the container to the analysis system in a sealed and preferably reversible manner. Preferably, the socket is in a sealed state when it is not connected and a passing state, allowing the homogenized mixture to pass through, once connected to the module. More preferentially, the socket allows a reversible connection, i.e. it once again becomes sealed when the module is disconnected. Thus, it is possible to change module in order to perform, for example, a confirmation measurement or another analysis or to take a sample while avoiding the risks of contamination. More particularly, the socket of the container consists for example of a female element, or respectively male element, intended to cooperate with a male element, or respectively female element, of a complementary socket located on the module. In one particular embodiment, the socket comprises a solid body which enables the flexible container to be grasped. Thus, the container can be easily handled by automated devices. Preferably, the handling of the bag is carried out by an automated device during at least one of steps a) to d), more preferentially at least during steps b) to d).

In one particular embodiment, the opening is equipped with connecting means and the socket is located on a stopper, itself equipped with connecting means capable of being and intended to be connected to the connecting means of the opening. The term "connecting means" is intended to mean any connector which makes it possible to physically link two elements to one another in a sealed manner and optionally in a reversible manner. They are generally formed from two complementary parts each placed on one of the elements intended to be linked to one another, these two complementary parts being capable of being and intended to be connected to one another. The connecting means may be mechanical connecting means, such as screw threads or attachment systems of clip type.

The container may comprise one or more filters on all or part of the surface. In particular, the filter is formed from a sheet sealed between the two sheets of plastic forming the container. The filter may also be formed from a pouch sealed to the container at the level of the opening. The filter separates the interior of the container into two volumes, with the first volume preferably opening out onto the opening and the second opening out onto the socket. The filter has a porosity sufficient to retain the solid particles. The filter preferably has a porosity of between 50 and 500 µm.

The homogenization step b) can be carried out mechanically by a homogenization apparatus or manually by pressing and shaking the container. A mechanical homogenization is particularly suitable for the analysis of essentially solid or pasty samples. Preferably, the homogenization is carried out by a mechanical homogenization apparatus well known to those skilled in the art, such as a Stomacher® bag. At the end of this homogenization step, the sample and the culture medium form a homogenized mixture also called suspension.

In order to be able to carry out this homogenization, the container comprises a homogenization zone. The term "homogenization zone" defines a zone of the container that is useful for homogenization, in particular mechanical homogenization by means of homogenization apparatuses of Stomacher® bag type. This homogenization zone is generally located in the lower part of the container, typically in the lower half, or even the lower third of the container. For example, the homogenization zone is defined by a rectangle, three of the sides of which correspond to the bottom of the container and to the lateral sides of the container, the fourth side corresponding to a straight line located 10 to 50 cm, preferably 15 to 40 cm above the bottom of the container. The surface area of the homogenization zone generally corresponds to 30% to 90%, preferably 50% to 80%, of the surface area of the flexible container. For example, for a container 15×10 cm±2 cm in size, the homogenization zone is 10×10±2 cm in size; for a container 30×19 cm±5 cm in size, the homogenization zone is 19×19±5 cm in size; and for a container 58×38±10 cm in size, the homogenization zone is 38×38±10 cm in size. Moreover, the homogenization zone preferably defines a volume greater than 90 $cm^3$ when the container is filled. For example, for a container 15×10 cm±2 cm in size, the homogenization zone preferably defines a volume of between 90 and 120 $cm^3$; for a container 30×19 cm±5 cm in size, the homogenization zone preferably defines a volume of between 220 and 280 $cm^3$; and for a container 58×38±10 cm in size, the homogenization zone preferably defines a volume of between 3370 and 3490 $cm^3$.

The socket of the flexible container must be located outside the homogenization zone. It can be located on the upper part or the lower part of the container. Preferably the socket is located in the upper part of the container above the homogenization zone, for example near the opening. The socket can be located on an appendage extending from one of the sides of the container. Although preferably located on one of the lateral sides of the container, the appendage may also be located on the bottom of the container. The socket may be isolated from the interior of the container by separation means. The separation means may consist of a device distinct from the container, such as a clamp or a rod, or may be integrated into the container, such as a zip or a zip fastening.

The closing of the flexible container at the end of step a) or b) can be carried out by any closing means which allows sealed or virtually sealed closure of the container. The term "virtually sealed closure" is intended to mean closure sealed in particular with respect to pathogenic agents but which can be substantially permeable to gases. The closing means can consist of a closing device distinct from the container, such as a clamp or a rod of the BagClip® type, sold by Interscience. They may also be integrated into the container. In this case, the closing means may be a zip or a zip fastening formed for example by a set of ribs and grooves placed on the internal surfaces of the bag at the level of the opening and intended to cooperate with one another so as to ensure sealed closure, as for example on the Minigrip bags sold by Flexico. The closing means may also consist of a stopper corresponding to the opening. In this case, the stopper and the opening preferably have connecting means capable of being and intended to be connected to one another. The closure may also be carried out by heat-sealing the walls of the container at the level of the opening.

The enrichment step c) consists in placing the flexible container containing the homogenized mixture under conditions which promote the development of the target analyte. Typically, the flexible container is placed in an incubator between 20 and 45° C., for conventional microbiology analyses.

A module is connected to the flexible container at the start, during or at the end of step c), i.e. before, during or after the enrichment. For this, the module according to the invention comprises a socket capable of being and intended to be connected with the socket of the flexible container. Once the sockets of the flexible container and of the module are connected to one another, the module can access the content of the flexible container. In other words, the flexible container and the module are in communication so that the homogenized mixture can pass freely from the interior of the container to the module, without opening the container. Preferably, the socket is positioned downwards when the analysis system is connected to the container. Thus, a change in configuration of the flexible container may be necessary in order for the homogenized mixture to be in contact with the socket. In particular, when the socket is located in the upper part of the container, it may be necessary to position the container substantially horizontally on one of the lateral sides, or even to completely turn the container over so that the homogenized mixture contained in the container comes into contact with the socket. In some cases, the module may also be connected to the flexible container before step a) or step b) provided that the module does not risk being damaged during the homogenization.

In step d), the analysis of the homogenized mixture is carried out by an analysis system. Preferably, the analysis is carried out continuously, i.e. in real time or at regular time intervals, for example during the enrichment. In this case, step d) can be carried out during step c).

In a first embodiment, the module comprises the analysis system or a part thereof. The analysis system can therefore be connected directly to the container via the socket of the module. The analysis system may be a spot analysis system. In this case, the module is preferably connected before or after the enrichment step. The analysis system may also be a continuous analysis system. In this case, the module is preferably connected to the container before the enrichment step and remains connected during the enrichment step.

In a second embodiment, the module comprises a collection system. Thus, a sample of the homogenized mixture is taken by the collection system while the module is connected to the flexible container, for the purpose of subsequent analysis by the analysis system. In this case, the collection system is preferably connected before or after the enrichment step, always without opening of the bag.

In these two embodiments, the analysis system may be any system which enables the analysis of a sample, in particular a biological, chemical, physicochemical or microbiological analysis. Preferably, the analysis system is a microbiological analysis system, in particular an agar medium inoculator, an automated molecular biology device, an automated immunoenzymatic analysis device, a mass spectrometer, a flow cytometer, an immunochromatographic test or an electrochemical, piezoelectric or optical sensor. The analysis system preferably implements an optical method enabling the direct detection of an analyte in real time without marker, such as surface plasmon resonance, methods based on interferometry or optical waveguides, or a quartz microbalance. To this effect, the analysis system advantageously comprises detection means. The analysis system may also comprise a film placed upstream of the detection means in order to protect the detection means from any deposits of solid particles. The anaylsis system may also comprise a measuring unit for measuring and optionally interpreting the signals detected by the detection means. In this case, the measuring unit may be distinct from the module according to the invention comprising the detection means.

In one particular embodiment, the detection means comprise one or more specific biosensors which enable the selective detection of a specific target analyte, in particular optical or electrochemical biosensors. In the present application, a biosensor consists of at least one ligand capable of detecting and/or interacting with an analyte, and transduction means which convert the chemical or biological signal into an easily interpretable physical signal. The transduction means may be based, non-exhaustively, on an electrochemical, optical, acoustic, calorimetric, electromagnetic or piezoelectric process. The biosensors may be functionalized with specific ligands in particular chosen from antibodies, aptamers, phage proteins, antigens, oligosaccharides and small organic molecules. For example, a biosensor as described in documents WO 2012/073202 or WO 2013/060989 may be used as detection means according to the invention. The biosensors may comprise several detection zones that can comprise different sensors. The various detection zones may be directed against the same target analyte or against different target analytes. One or more detection zones may also serve as a reference (negative control).

The target analyte may be chosen from bacteria and also proteins, polysaccharides, fatty acids and nucleic acids of which they are composed or which they emit. Preferably, the target analyte is chosen from pathogenic bacteria such as *Salmonella, Listeria* and enterohemorrhagic strains of *Escherichia coli* and protein metabolites thereof, in particular protein toxins thereof.

In one particular embodiment, the detection means are located directly on the socket of the module so that, when the module is connected to the container, the detection means are inside or in direct communication with the inside of the container. Thus, the analysis step can be carried out directly in the container. Preferably, the socket of the module comprises a shaft on which the detection means are located, and which penetrates inside the container once the module is connected to the container. During the analysis step, the container is positioned so that the detection means are at the center of the homogenized mixture. Thus, contact of the detection means with the solid particles which sediment or flow on the surface can be avoided.

In one particular embodiment, the container may comprise several sockets for enabling for example a connection of several analysis systems and carrying out several analyses simultaneously on the same homogenized mixture.

In another particular embodiment, the analysis system may be simultaneously connected to several containers in order to enable for example an analysis of several homogenized mixtures.

Furthermore, when the measuring unit is distinct from the module comprising the detection means, the measuring unit may be shared by several modules. It is thus possible to carry out the analysis of several samples continuously with one measuring unit, said unit carrying out measurements sequentially at regular time intervals with each of the modules.

According to another embodiment, several containers are connected to a single module enabling simultaneous analysis of the mixtures contained in each of the containers.

The method according to the invention is particularly suitable for the analysis of a sample that is at least partly solid or pasty, requiring mechanical homogenization. In one preferred embodiment, the method of analysis of a sample according to the invention comprises:
  a) the introduction of the sample and of a culture medium into a flexible container;
  b) the manual or mechanical homogenization of the sample by a homogenization apparatus so as to obtain a homogenized mixture of the sample in the culture medium;
  c) the enrichment of the homogenized mixture; and
  d) the analysis of the homogenized mixture by an analysis system,
characterized in that
steps a) to d) are carried out in a single container;
the flexible container is closed at the end of either of steps a) and b);
the analysis system is directly connected to the flexible container before step c); and
steps c) and d) and the connecting of the analysis system to the flexible container are carried out without requiring reopening of the container.

More preferentially, the present invention relates to a method of microbiological analysis of a sample by detection of an analyte, comprising:
  a) the introduction of the sample and of a culture medium into a flexible container;
  b) the manual or mechanical homogenization of the sample and of the culture medium by a homogenization apparatus so as to obtain a homogenized mixture;
  c) the enrichment of the homogenized mixture; and
  d) the analysis of the homogenized mixture by an analysis system comprising detection means;
characterized in that
steps a) to d) are carried out in a single container;
the flexible container is closed at the end of either of steps a) and b);
the analysis system is directly connected to the flexible container at the start of step c);
the homogenized mixture is in contact with the detection means during step c) and the analysis of the homogenized mixture is carried out continuously during step c); and
steps c) and d) and the connecting of the analysis system to the flexible container are carried out without requiring reopening of the container.

The present invention also relates to a flexible container as described above. The flexible container according to the invention comprises a homogenization zone, an opening and a socket, said socket being located outside the homogenization zone. Typically, the flexible container has an essentially rectangular shape defined by a top side comprising the opening, two lateral sides adjacent to the top side, and a bottom opposite the top side. The homogenization zone is generally located in the lower part of the container. It corresponds for example to a rectangle representing 30% to 90%, preferably 50% to 80%, of the surface area of the flexible container, one of the sides of the homogenization zone preferably being joined to the bottom of the container. The socket is located outside the homogenization zone. It is generally located on one of the top or lateral sides or on the bottom of the container. Preferably, the socket is located on one of the lateral sides of the container, in proximity to the top side. In one particular embodiment, the opening of the container is equipped with connecting means and the socket is located on a stopper equipped with connecting means capable of being and intended to be connected to the connecting means of the opening.

In one particular embodiment, the socket comprises a solid body which enables the flexible container to be grasped. Thus, the container can be easily handled by automated devices. Consequently, the present invention also relates to the use of at least one flexible container in an analysis method, characterized in that the handling of said flexible container is carried out by an automated device.

FIGS. 1*a* to 1*e* illustrate various embodiments of the container according to the invention. The flexible container 100, formed from two flexible plastic sheets of essentially rectangular shape sealed to one another, has an opening 101 on the top side of the bag, a bottom 102 opposite the opening 101 and two lateral sides 103 and 104. The flexible container comprises a homogenization zone 105 intended to enable the homogenization of its content, in particular by a mechanical homogenization apparatus.

In a first embodiment, the homogenization zone 105 is located in the lower part of the container 100. It covers an essentially rectangular zone extending in a first direction from a lateral side 103 to the other lateral side 104 of the container 100, and in the second direction from the bottom of the container 104 to an upper limit located for example at a distance of between 10 and 50 cm from the bottom of the container. In a first alternative illustrated by FIG. 1*a*, the container 100 comprises a socket 106 located in the upper part of the lateral side 103, above the homogenization zone 105. In a second alternative illustrated by FIG. 1*b*, the container 100 comprises a truncated corner 107 between the side of the opening 101 and one of the lateral sides 103, the truncated corner 107 being above the homogenization zone 105. A socket 106 is located on the truncated corner 107. The container 100 also comprises a filter 108 sealed on for example at the level of the opening 101, the filter separating the interior into two volumes, the first opening out on the opening 101 and the second opening out on the socket 106. In a third alternative illustrated by FIG. 1*c*, the container 100 comprises an appendage 109 on one of the lateral sides 103. The appendage can be located in the lower part of the container in proximity to the bottom of the container 102. A socket 106 is located on the appendage 109. The appendage can be isolated from the interior of the container by separating means (not represented). The container may comprise a filter (not represented). The filter may be sealed on for example at the level of the opening 101, as illustrated in FIG. 1*b*, or may be located at the inlet of the appendage 109.

Figure 1A:
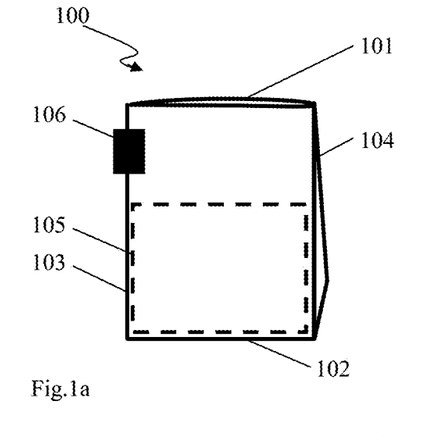
FIGS. 1a to 1e represent various embodiments of the flexible container according to the invention.
Figure 1B:
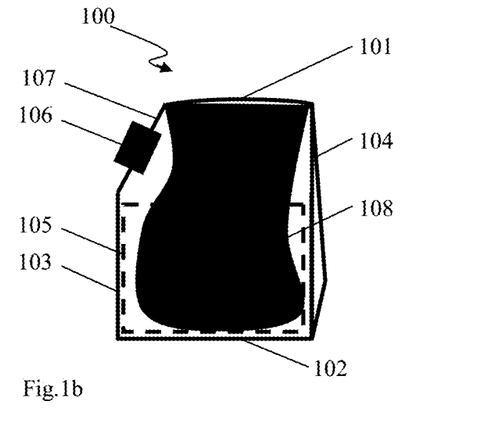
Figure 1C:
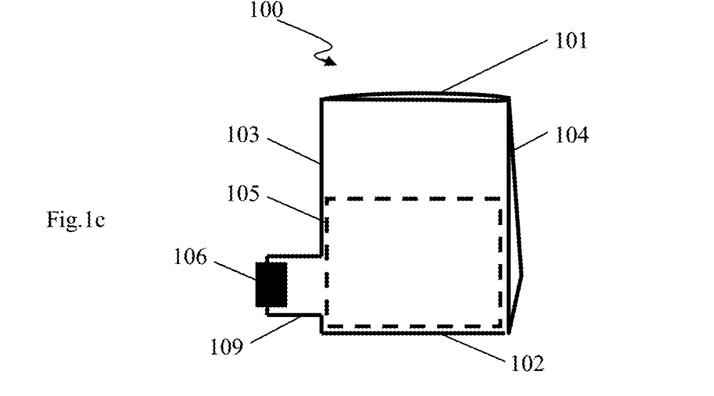
Figure 1D:
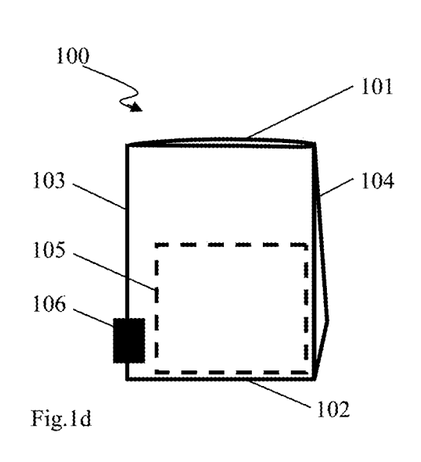

In a second embodiment illustrated by FIG. 1*d*, the homogenization zone 105 is located in the lower part of the container 100. It covers a zone essentially as described in the first embodiment but excludes one of the lateral sides 103. A socket 106 is located on the lateral side 103 outside the homogenization zone 105. The container may comprise a filter (not represented) as illustrated in FIG. 1*b*.

Figure 1E:
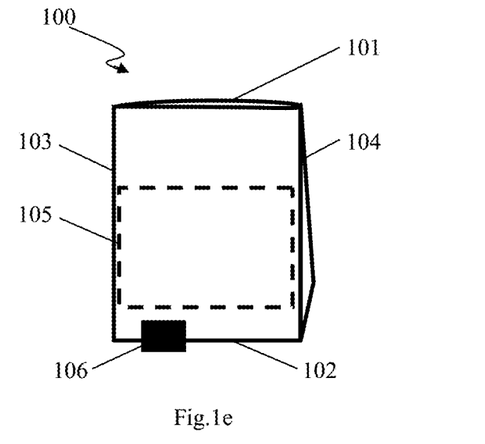

In a third embodiment illustrated by FIG. 1e, the homogenization zone 105 is located above the bottom of the container 102. It covers an essentially rectangular zone extending in a first direction from a lateral side 103 to the other lateral side 104 of the container 100, and in the second direction to a height of between for example 10 and 50 cm. A socket 106 is located on the bottom of the bag 102, outside the homogenization zone. The container may comprise a filter (not represented) as illustrated in FIG. 1b.

The container according to the invention has the advantage of not modifying the procedures used in test laboratories, in particular from the point of view of the preparation of the sample, while at the same time dispensing with the reopening of the container at the end of the enrichment, thus preventing any contamination of the working environment and of the operators.

Figure 2A:
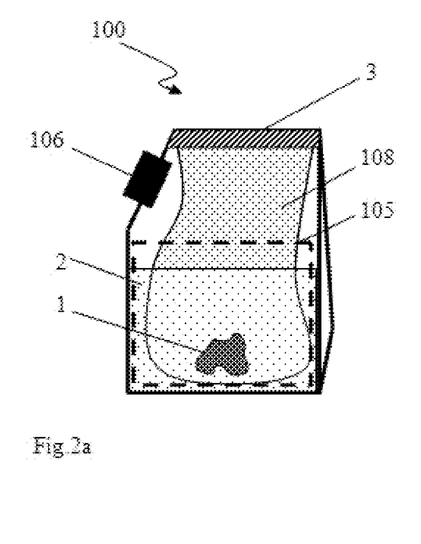
FIGS. 2a to 2e, 3 and 4 illustrate the implementation of the method according to the invention.
Figure 2B:
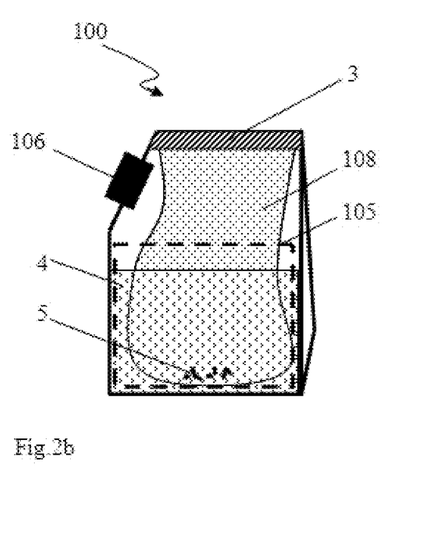
Figure 2C:
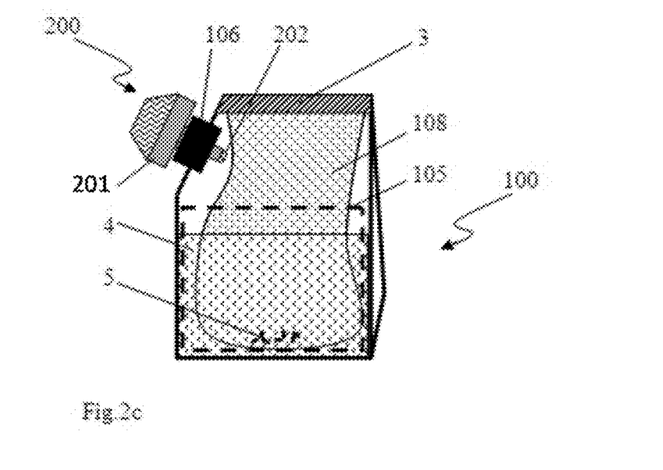
Figure 2D:
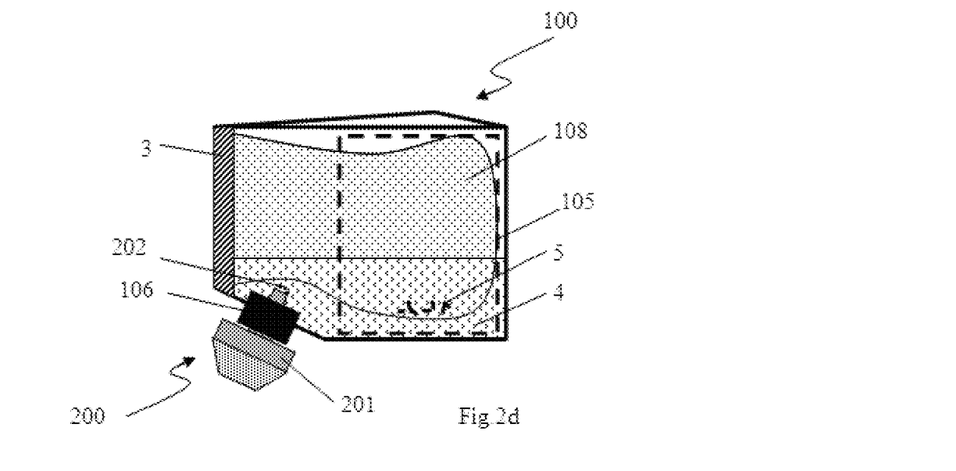
Figure 2E:
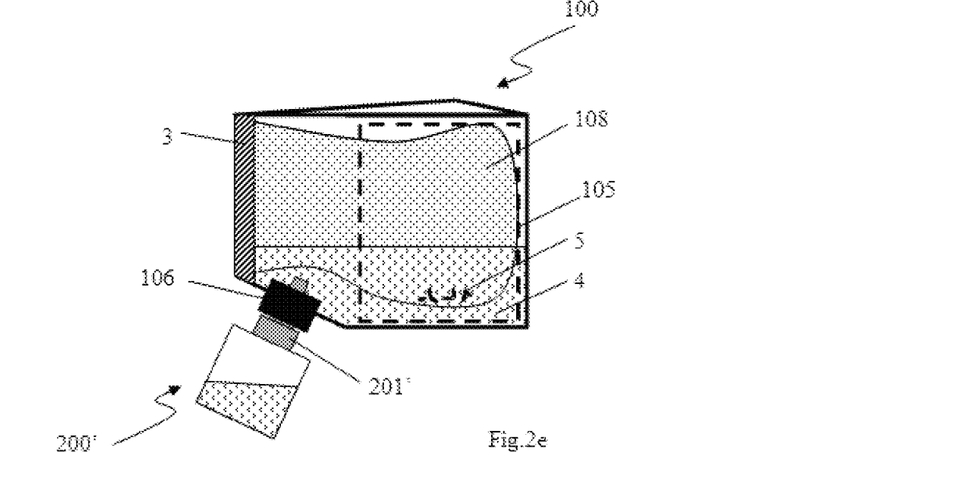

The flexible container according to the invention is suitable for the analysis method according to the invention. FIGS. 2a to 2e illustrate an example of implementation of the method according to the invention. After step a), the container 100 contains a solid or semi-solid sample 1 and the culture medium 2, and is closed by a seal 3. It is in the vertical position such that the sample 1 and the culture medium 2 are in the homogenization zone 105, in the lower part of the container 100 (FIG. 2a). After the homogenization step b), the sample 1 and the culture medium 2 form a homogenized mixture 4. The residual particles 5 resulting from the milling of the sample 1 are retained by the filter 108 (FIG. 2b). It should be noted that the seal 3 could very easily have been made after step b) and not after step a). The socket 201 of a module 200 comprising an analysis system with detection means 202 is connected to the socket 106 of the container 100 at the start of step c) (FIG. 2c). In FIG. 2c, the detection means are located inside the container when the analysis system is connected to the container. Alternatively, the detection means may be located in a compartment of the analysis system which remains outside the container but is in direct communication with the interior of the container when the analysis system is connected to the container. In order to enable the continuous analysis of the suspension 4 during the enrichment step c), the container 100 is positioned so as to enable the homogenized mixture to be in contact with the detection means 202. For example in FIG. 2d, the container is positioned horizontally on the lateral side 103 adjacent to the socket 106. Alternatively, the container may be turned over by 180°, the seal 3 being downward. When the analysis is finished, the module 200 comprising the analysis system can be replaced with a module 200' comprising a collection system (FIG. 2e). Thus, a fraction of the enriched homogenized mixture can be sampled in order to confirm the result by means of another confirmation analysis method, this being without it having been possible for the operators handling the containers to be in contact with the enriched mixture potentially contaminated with pathogenic microorganisms.

More specifically, a container according to FIG. 1a can be used for the analysis of 25 ml of raw milk. The container has for example the general shape of a rectangle 17 cm wide and 32 cm high (FIG. 1a). The homogenization zone 105 measures 17*18 cm. The socket 106 is located more than 18 cm from the bottom 102.

The protocol of such an analysis comprises:
the introduction of 25 ml of raw milk and of 225 ml of buffered peptone water into the container;
the manual kneading or the mechanical homogenization of the homogenization zone 105 in order to obtain a homogenized mixture;
the closing of the container using a rod or by sealing;
the rotation of the container by 90° so as to position the lateral side 103 downward in order to bring the homogenized mixture into contact with the socket;
the connection of a module to the socket of the container, said module comprising a biosensor for the real-time detection of *Salmonella* and enterohemorrhagic *Escherichia coli*. The biosensor may be, for example, a biosensor such as that described in document WO 2013/060989, functionalized with anti-*Salmonella*, anti-enterohemorrhagic *Escherichia coli* and anti-rabbit IgG ligands (the latter being used as a negative control);
the enrichment of the homogenized mixture by placing the container in a thermostatted chamber at 41.5° C.; and
the real-time analysis of the *Salmonella* and enterohemorrhagic *Escherichia coli* by optical reading using as a basis the physical phenomenon of surface plasmons as described in document EP 2 646 565.

Likewise, a container according to FIG. 1b can be used for the analysis of 375 g of minced meat. Such a container has for example a rectangular general shape that is 38 cm wide and 55 cm high, truncated on one of its upper corners. The truncated corner 107 measures 18 cm, the top side comprising the opening 101 measures 29 cm and the lateral side 103 adjacent to the truncated corner measures 40 cm. The socket 106 is located on the truncated corner 107, 8 cm from the opening 101, and the homogenization zone 105 measures 38×38 cm. A filter with a porosity of 250 μm separates the container into two volumes, the first opening out on the opening and the second opening out on the socket. The protocol for such an analysis comprises:
the introduction of 375 g of minced meat and of 3375 ml of buffered peptone water into the container;
the kneading of the homogenization zone using a paddle kneader of Stomacher® type for 60 seconds in order to obtain a homogenized mixture;
the closing of the container in a sealed manner by sealing the opening such that the socket is located between 2 and 10 cm from the seal;
the connection of a module to the socket of the container, said module comprising a biosensor for the real-time detection of *Salmonella* and enterohemorrhagic *Escherichia coli;*
the rotation of the container by 180° so as to position the top side comprising the opening 101 downward in order to bring the homogenized mixture into contact with the socket 106 located on the truncated corner 107 in order to collect a fraction of the enriched homogenized mixture;
the enrichment of the homogenized mixture by placing the container in a thermostatted chamber at 41.5° C.;
the real-time analysis of the *Salmonella* and enterohemorrhagic *Escherichia coli;*
in the case of a positive result, the disconnection of the module comprising the analysis system and the connection of a module comprising a collection system for collecting a fraction of the enriched homogenized mixture;
the analysis of the fraction of enriched homogenized mixture by PCR or any other rapid method of detecting pathogens in order to confirm the detection of the *Salmonella* and/or enterohemorrhagic *Escherichia coli*.

Figure 3:
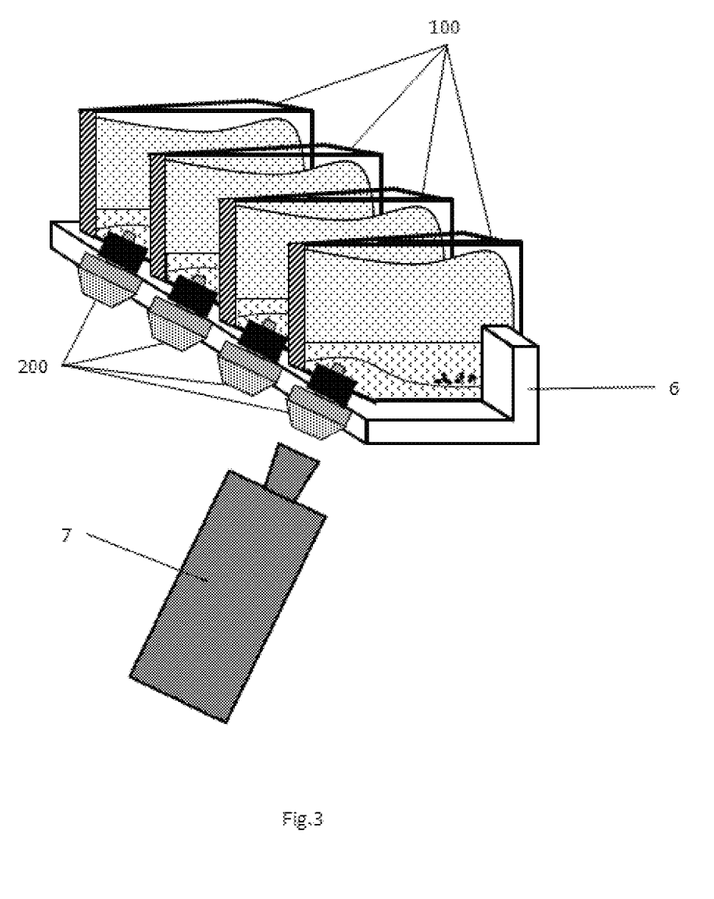

Moreover, FIG. 3 illustrates an analysis system for monitoring the analysis at regular intervals of several containers simultaneously. In FIG. 3, modules 200 comprising detection means (not represented) are connected to each of the flexible containers 100. The flexible containers 100 are arranged on a mobile support 6 which sequentially presents each of the modules 200 to a measuring unit 7 for a period of time sufficient to allow the measuring unit 7 to perform a measurement.

Figure 4:
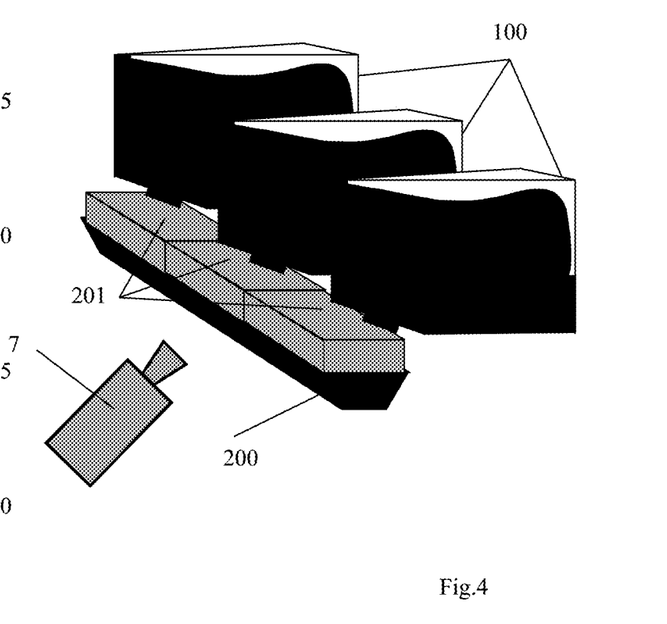

According to another embodiment, FIG. 4 illustrates an analysis system enabling the simultaneous analysis of several containers 100 connected to the same module 200 comprising several sockets 201 and detection means 202 (not represented) distributed in as many distinct zones and without physical communication. Thus, the mixture from each container 100 is connected to a single zone comprising detection means 202 (not represented) and the analysis is carried out independently for each of the containers. A measuring unit 7 then makes it possible to independently but simultaneously analyze the homogenized mixture of each of the containers.

Thus, several containers connected to the same common module according to FIG. 4 can be used for the analysis of 25 g of minced beef. The containers have for example a rectangular general shape which is 19 cm wide and 35 cm high. The socket 106 is located on the side 103, more than 26 cm from the bottom 102. The module 200 comprising the analysis system carries for example three sockets 201 capable of being and intended to be connected with the sockets 106 of the three containers. Each of the three sockets communicates independently with detection means 202 (in this case, antibodies directed against *Salmonella* spp and *Escherichia coli* O157:H7 and against rabbit IgGs).

The protocol for such an analysis comprises:
- the introduction into three containers (A, B, C) of 25 g of sample of minced beef and of 225 ml of buffered peptone water;
- the inoculation of the container A with 10 cfu (colony forming units) of *Salmonella typhimurium* and the inoculation of the container B with 3 cfu (colony forming units) of *Escherichia coli* O157:H7 (the container C does not receive microbial culture);
- the kneading of the homogenization zones of each of the containers using a paddle kneader of Stomacher® type for 60 seconds in order to obtain homogenized mixtures;
- the closing of the containers by sealing;
- the rotation by 180° of each of the containers so as to position the bottoms 102 upward in order to bring the homogenized mixtures into contact with the sockets 201;
- the connection of the sockets of the containers to a common module 200, said module comprising detection means 202 (biosensors) for the real-time detection of the *Salmonella* spp. and *Escherichia coli* O157:H7;
- the enrichment of the homogenized mixtures by placing the connected containers in a chamber thermostatted at 37° C.; and
- the real-time analysis of the *Salmonella* spp. and of the *Escherichia coli* O157:H7 by a surface plasmon resonance imaging method as described in document EP 2646565.

Figure 5A:
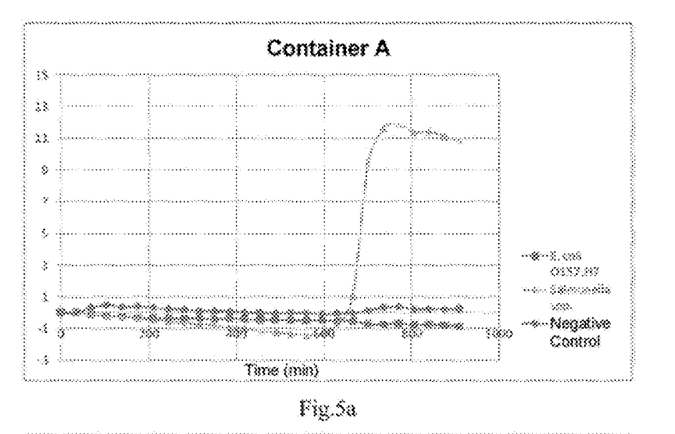
FIGS. 5a to 5c represent results obtained for the simultaneous search for *Salmonella* spp and *Escherichia coli* O157:H7 in three samples of minced beef contained in containers A, B, and C, said containers containing respectively *Salmonella* spp., *Escherichia coli* O157:H7 and no contaminant.
Figure 5B:
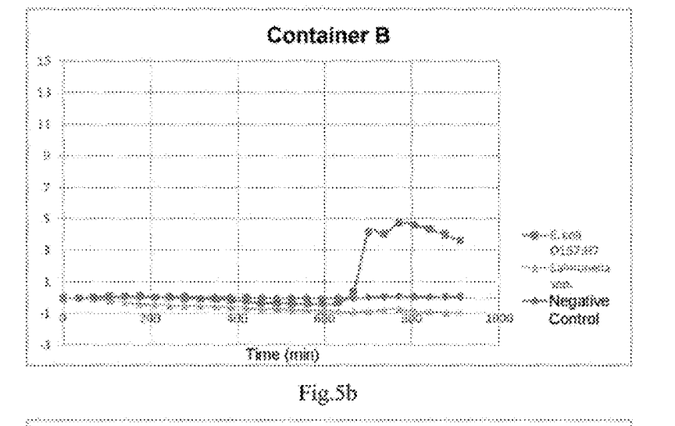
Figure 5C:
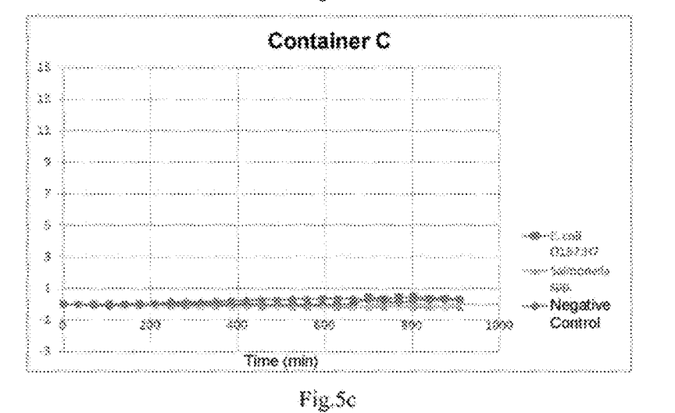

The results obtained for the search for *Salmonella* spp and *Escherichia coli* O157:H7 for the three samples of minced beef of the containers A, B, and C are represented in FIG. 5*a*, FIG. 5*b* and FIG. 5*c* respectively. It is observed therein that the detection means made it possible to carry out detections of various microorganisms in parallel, in each of the containers simultaneously.

The present invention also relates to an analysis kit comprising the flexible container and a module, as described above.

According to the invention, the analysis kit comprises:
- at least one flexible container comprising a homogenization zone, an opening and a socket, said socket being located outside the homogenization zone;
- a module comprising a socket capable of being and intended to be connected with the socket of the flexible container.

The module is preferably a detection module comprising detection means as defined above. The detection means enable for example the selective detection of at least one target analyte chosen from bacteria and proteins. Alternatively, the module may be a collection module comprising a collection system as defined above.

The kit according to the invention can be used for the microbiological analysis of a sample, in particular in the food-processing field, the environmental field or the health field. The kit according to the invention is particularly suitable for the analysis of a solid or semi-solid sample requiring a mechanical homogenization step, in particular by implementing the method according to the invention.

The present invention makes it possible to perform all the preparation (in particular homogenization), enrichment and optionally analysis steps in a single flexible container and without opening the container.

According to one particular embodiment, it also makes it possible to independently and simultaneously analyze the homogenized mixture in several containers through the use of a single module.

Thus, not only are the risks of contamination reduced, but the implementation of the analysis is simplified owing to the reduction in the number of operations required. This simplification enables easier automation of the analysis. In one particular embodiment, the kit according to the invention also makes it possible to carry out the analysis in real time during the enrichment step. This decreases the time required for a positive response, which can be obtained as soon as the presence of the target analyte is detected. Finally, since the analysis system is provided separately from the flexible container, it is possible to choose the analysis system suitable for the target analyte sought or optionally to change the analysis system for example in order to confirm a positive result without reopening the container.

The invention claimed is:

1. A method of analysis of a sample comprising:
a) introducing the sample and a culture medium into a single, flexible container having a single compartment;
b) homogenizing the sample and the culture medium so as to obtain a homogenized mixture;
c) closing said container after step a) or step b);
d) enriching the homogenized mixture;
e) connecting a module to the flexible container before, during or after step d); and
f) analyzing homogenized mixture by an analysis system, wherein the module comprises the analysis system; and wherein steps a) to d) are carried out in the single container; and steps d) to f) are carried out without reopening of the container.

2. The method of claim 1, wherein the analysis is a microbiological analysis.

3. The method of claim 1, wherein the flexible container comprises a homogenization zone, an opening and a socket, said socket being located outside the homogenization zone; and the module comprises a socket adapted to be connected with the socket of the flexible container.

4. The method of claim 3, further comprising changing the conformation of the flexible container after closure thereof and before step f) in order for the homogenized mixture to be in contact with the socket adapted to be connected with the socket of the module.

5. The method of claim 3, wherein the socket of the flexible container is sealed when it is not connected and is adapted to allow the homogenized mixture to pass through when it is connected to the socket of the module.

6. The method of claim 1, wherein the analysis system comprises a detector enabling the selective detection of at least one target analyte chosen from bacteria and/or proteins.

7. The method of claim 6, wherein the detector is a specific optical or electrochemical biosensor functionalized with specific ligands.

8. The method of claim 1, wherein the sample is solid or semi-solid.

9. The method of claim 7, wherein said specific ligands include antibodies, aptamers and phage proteins, oligosaccharides or small organic molecules.

10. The method of claim 1, wherein step b) comprises homogenizing mechanically by a homogenization apparatus or manually by pressing and shaking the container.

* * * * *